United States Patent [19]
Wainer et al.

[11] Patent Number: 6,037,337
[45] Date of Patent: Mar. 14, 2000

[54] USE OF THE ENANTIOMERS OF IFOSFAMIDE IN ANTITUMOR THERAPY FOR REDUCING SIDE EFFECTS

[75] Inventors: Irving William Wainer; Camille Pierre Granvil; Gerald Batist; Julie Ducharme, all of Quebec, Canada; Helen Frances Baker, Cambridge, United Kingdom

[73] Assignee: Darwin Discovery Limited, United Kingdom

[21] Appl. No.: 09/046,066

[22] Filed: Mar. 23, 1998

Related U.S. Application Data

[63] Continuation of application No. 08/605,179, Jun. 10, 1996, abandoned, which is a continuation of application No. PCT/GB94/02171, Oct. 5, 1994.

[30] Foreign Application Priority Data

Jun. 23, 1994 [GB] United Kingdom .................... 9412689

[51] Int. Cl.[7] ...................................... A61K 31/66
[52] U.S. Cl. .............................................. 514/110
[58] Field of Search ............................... 514/110

[56] References Cited

PUBLICATIONS

Kleinrok, Zdzislaw et al. (1986) "Pharmacological evaluation of ifosfamide and its enantiomers in laboratory animals," *Arch. Immunol. Ther. Exp.*, vol. 34, pp. 293–304.

Kusniercyzk, H. et al. (1986) "Antitumor activity of optical isomers of cyclophosphamide, ifosfamide and trofosfamide as compared to clinically used racemates," *J. Immunopharmacol.*, vol. 8, pp. 455–480.

Wainer, I.W. et al. (1994) "Efficacy and toxicity of ifosfamide stereoisomers in an in vivo rat mammary carcinoma model," *Cancer Res.*, vol. 54, pp. 4393–4397.

Masurel, Dominique et al. (1990) "Efficacy, toxicity, pharmacokinetics, and in vitro metabolism of the enantiomers of ifosfamide in mice," *Cancer Res.*, vol. 50, pp. 252–255.

B. Testa et al. (1990) "Racemates Versus Enantiomers in Drug Development: Dogmatism or Pragmatism?" *Chirality*, vol. 2, pp. 129–133.

Blaschke, G. et al. (1986) "Preparative isolation and pharmacological–toxicological studies of the enantiomers of ifosfamide," *Arzneim.–Forsch.*, vol. 36, pp. 1493–1495.

*Primary Examiner*—Jerome D. Goldberg

[57] ABSTRACT

(R)-Ifosfamide is administered as a cytotoxic drug, in order to minimize side effects. (S)-Ifosfamide may be administered subsequently.

1 Claim, 1 Drawing Sheet

USE OF THE ENANTIOMERS OF IFOSFAMIDE IN ANTITUMOR THERAPY FOR REDUCING SIDE EFFECTS

CROSS-REFERENCE TO RELATED APPLICATION

This application is a continuation of application Ser. No. 08/605,179, filed Jun. 10, 1996, now abandoned, which is a continuation of PCT/GB94/02171, filed Oct. 5, 1994.

FIELD OF THE INVENTION

This invention relates to ifosfamide and its therapeutic use.

BACKGROUND OF THE INVENTION

Ifosfamide is a cytotoxic alkylating agent. It has a similar spectrum of activity to cyclophosphamide. It has been shown to be more effective and less toxic than cyclophosphamide when given by pulsed or infusional regimes. The compound is licensed for use in refractory testicular cancer in the U.S., and for tumors of lung, ovary, cervix, breast and testis and soft tissue sarcoma in the UK. It is used as a single agent and in combination with radiotherapy, surgery and other cytotoxic agents.

Ifosfamide is a cytotoxic compound and effects other than the antitumor effect are expected. Myelosuppression, alopecia, nausea and vomiting are all unwanted effects of the compound.

The compound has other unwanted toxicities, e.g. on the urinary tract, and neurotoxicity, which limit the dosing and make the compound difficult to use. Combination with the uroprotective agent mesna has reduced the incidence of haemorrhagic cystitis, but nephrotoxicity is a potentially serious side-effect.

Neurotoxic effects range from mild somnolence to severe encephalopathy, hallucinations and coma. In most cases, they are reversible, but in some they are not. They are more prevalent after oral dosing and large single IV doses. It is thought that they are caused by a metabolite, possibly chloroacetaldehyde. This is a significant problem: the drug must be administered in hospital because of the occurrence of these side-effects.

CNS side-effects were a major dose-limiting side-effect when the compound was in development as an oral formulation. The side-effects appeared at a much lower dose than they did during iv administration, and this meant that cytotoxic doses could not be reached. It is known that there is much more metabolism of the compound after oral dosing; in particular, higher levels of chloroacetaldehyde are produced, indicating more N-dechloroethylation.

Ifosfamide is a chiral compound. Its enantiomers dexifosfamide (herein sometimes "(R)-IFF") and levoifosfamide (herein sometimes "(S)-IFF") are known, and may be prepared by classical resolution. Processes for their preparation are described in U.S. Pat. No. 4,684,742, Polish Patent No. 119,971, and British Patent No. 1,553,984.

Ifosfamide requires metabolic activation. One of the two main metabolic pathways produces the active species, the isophosphoramide mustard. The 4-hydroxy-ifosfamide may also be an active species. The second main pathway, N-dechloroethylation, produces 2 and 3-dechloro metabolites, with the release of chloroacetaldehyde. S-Ifosfamide produces R-3-dechloroifosfamide (R-3DCE) and S-2-dechloroifosfamide (S-2DCE). R-ifosfamide produces S-3-dechloroifosfamide (S-3DCE) and R-2-dechloroifosfamide (R-2DCE). Other metabolic routes are responsible for a very small amount of the total metabolism. Metabolism is induced by dividing the dose over several days; the main increase being in the route to the mustard. On a single dose, between 20–40% of the drug is excreted unchanged, and 15–50% of the compound is metabolised through the N-dechloroethylation pathway.

Boos et al, Cancer Chemother. Pharmacol. 28:455–460 (1991), investigated the urinary excretion of the enantiomers of ifosfamide, following administration of the racemate. It was concluded that "Theoretically, an advantage in the form of reduced side-chain metabolism could be expected from the use of the S form of ifo in nearly half of our patients and the R form in the other half", and "stereospecific metabolism does not indicate that any clear-cut advantage can be gained from the application of an individual enantiomer."

Masurel et al, Cancer Res. 50: 252–255 (1990), studied the efficacy and toxicity of IFF enantiomers in CBA/CaJ mice. The results indicated that there were no statistically significant differences between the efficacies of (R)-IFF, (S)-IFF, and (R,S)-IFF against childhood rhabdomyosarcoma (HxRh28) grown in vivo as a xenograft in immunoincompetent female CBA/CaJ mice. The same was true regarding the acute toxicities of the stereoisomers. No statistically significant differences were found in the plasma pharmacokinetics of (S)-IFF, or in the in vitro N-dechloroethylation.

SUMMARY OF THE INVENTION

Surprisingly, it has been found that dexifosfamide gives reduced side-effects. This is based on the results of the analysis of the urine of 11 patients who received a 3 hour infusion of racemic ifosfamide. Patients had not received chemotherapy for a year and ifosfamide was the only drug administered during the pharmacokinetic study. It is clearly shown in all patients that the side-chain metabolites come from S-ifosfamide more than from R-ifosfamide. There is also evidence to suggest that R-ifosfamide is more myelotoxic in the Fischer rat. This is suggestive of R-ifosfamide producing more of the mustard. The same results show that there is a trend to the R-isomer being more effective in treating the tumors in the rats.

Further, the results of incubating racemic ifosfamide with human liver microsomes, and measuring the 2 and 3-dechlorometabolites using chiral assays, show that the S-ifosfamide produces greater amounts of these metabolites than the R-ifosfamide. The results are broadly the same when the experiments were carried out separately with R and S-ifosfamide.

These data taken together show that, on a single dose, R-ifosfamide will produce less of the metabolites for the N-dechloroethylation pathway and is thus likely to produce lower levels of the CNS side-effects. The rat data are more meaningful that existing information obtained by Masurel et al; the mouse is not a satisfactory model, since the human pharmacokinetics and metabolism of ifosfamide are enantioselective.

Another aspect of the invention is based on an appreciation of the relative effects of the enantiomers of ifosfamide. The undesirable effect of administering levoifosfamide may be due to its quicker induction of undesirable metabolites, an effect which is reduced with time, while the corresponding effect of administering dexifosfamide increases more slowly. For longer-term administration of ifosfamide, therefore, it may be preferred to use a combination therapy, i.e. dexifosfamide initially, and levoifosfamide thereafter.

BRIEF DESCRIPTION OF THE DRAWINGS

FIG. 1A shows WBC results, and FIG. 1B the effect of treatment on platelets. There were 3–5 animals in each group. The following abbreviations etc. apply:

Figure 1A:
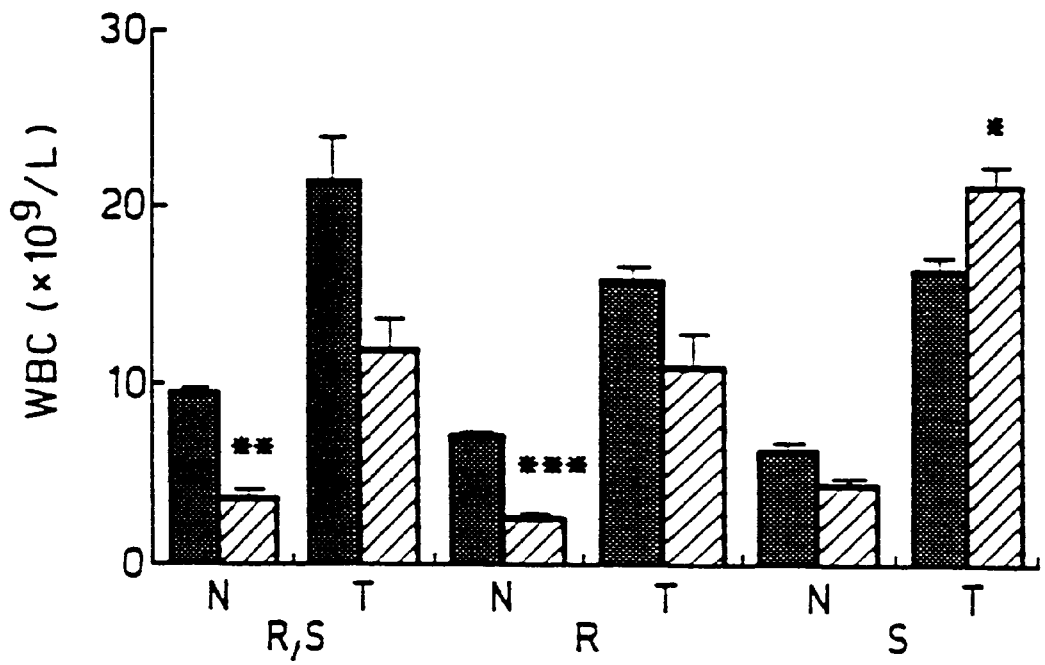
FIGS. 1A and 1B show peripheral blood counts obtained in tumor-bearing rats that received saline or ifosfamide treatment.

T: tumor-bearing heavy columns: controls shaded columns: groups treated with (R,S)-IFF, (R)-IFF or (S)-IFF

*: P<0.05

**: P<0.01

***: P<0.001

A versus B, P<0.05

C vesus D, P<0.01

DESCRIPTION OF THE INVENTION

The present invention is based on the discovery that the known side-effects can be reduced by the administration of enantiomeric ifosfamide. The desired enantiomer is substantially free of the other enantiomer and is preferably in an enantiomeric excess of at least 60% and more preferably at least 80%, most preferably 90% or more.

The drug used in this invention may be formulated in conventional media. It may be administered orally or by intravenous infusion. The formulation may include any suitable carrier. Such administration of the drug may avoid hospitalisation.

Especially for the novel combined therapy, discrete unit dosage forms may be provided. For example, "blister packs" of such unit dosages may be used, e.g. of tablets, capsules, vials, ampoules and the like. An integral package or "kit" of the dosages may be provided with instructions or coding, to indicate the appropriate order of administration.

The ifosfamide enantiomer used in the invention is administered in an amount determined by the nature of the tumor and the skill of the physician, such as 100 to 5000, e.g. 600, mg/m$^2$ per day/single dose; see also De Kraker, Anticancer Drugs 2:339–341 (1991), the contents of which are incorporated herein by reference. An advantage of the present invention is to allow higher/more frequent dosing, e.g. by a factor of 1.5, 2 or more. The frequency and duration may be determined by similar consideration.

The invention is based on a comparison of the metabolism of R-ifosfamide with that of the racemic compound and measurement of certain metabolites. By means of the invention, active rather than toxic metabolites are preferentially obtained in vivo.

In a first investigation, the stereoselective urinary excretion of the parent drug, i.e. racemic ifosfamide, and its metabolites, was investigated. This followed a single dose of ifosfamide in 7 female cancer patients, while monitoring for CNS toxicity.

The patients were chemotherapy-free for at least 1 year and did not exhibit impaired renal function or hypoalbuminaemia. Patients received a 3 h infusion of ifosfamide (3 g/m$^2$) with mesna uroprotection, total urine output was collected for 27 h, and urine samples were analysed by enantioselective gas chromatography, as described by Granvil et al, J.Chromatogr. 622:21–31 (1993).

One patient had a severe neurotoxic syndrome, with somnolence, dizziness, lethargy, tremors, and hallucinations. Since ifosfamide was the sole anti-cancer drug administered for the first chemotherapy cycle, toxicity data were not confounded by the effects of other anti-neoplastic agents.

A non-stereoselective analysis of urinary excretion data showed that the affected patient had the highest urinary concentrations of ifosfamide and dechloroethylated metabolites, although the high interpatient variability precluded any definite conclusion. Conversely, a stereoselective analysis, separating metabolites originating from R-ifosfamide (R-2DCE and S-3DCE) or S-ifosfamide (S-2DCE and R-3DCE) displayed very little variability for 6 of 7 patients. The other patient, who experienced severe neurotoxicity, showed much higher excretion of dechloroethylated metabolites from S-ifosfamide. In patients with excessive N-dechloroethylation, R-ifosfamide could have an improved efficacy/toxicity.

In order to help clarify the relative efficacies and toxicities of (S)-IFF and (R)-IFF, the effect of these enantiomers in F344 rats was investigated. Both non-tumor-bearing animals and those bearing a MatB rat mammary carcinoma were used in this study. The relative lethality, bone marrow suppression, weight loss, antitumor activity, and pharmacokinetics were determined for (R)-IFF, (S)-TFF and (R,S)-IFF. The results of these studies are presented below.

Chemicals (R,S)-Ifosfamide was supplied from Bristol-Myers Canada (Belleville, Ontario, Canada) and individual enantiomers were prepared by enantioselective high pressure liquid chromatography. The purity of each enantiomer was >99.5%. All other reagents and solvents were analytical grade. Stock solutions of IFF and hexobarbital (IS) were prepared in methanol at a concentration of 1 mg/ml and diluted to make calibration standards. These solutions were stored at −20° C. until used.

Gas Chromatography-Mass Spectrometry

The analysis of IFF in plasma was performed using gas chromatography-mass spectrometry. The gas chromatography was a Varian 3400 gas chromatograph equipped with a Finnigan A 200S gas chromatograph autosampler operating in the splitless mode. The mass spectrometer was a Finnigan Mat Model Incos 50 operating in the electron impact and selective ion monitoring mode. The chromatographic separation was carried out on a fused silica capillary column (DB-5; 30 m×0.25 mm, inside diameter; film thickness, 0.25 $\mu$m). The column oven temperature was linearly programmed from 80° C. to 250° C. The injector temperature was 250° C. in the splitless mode, the helium pressure was 8 psi, and the transfer line was maintained at 260° C. The mass spectrometer was operated in the electron impact ionization mode at an ion source temperature of 180° C. and an ionization energy of 70 eV.

Plasma Preparation

To 0.1 ml of plasma sample were added 20 $\mu$l IS (hexobarbital, 100 $\mu$g/ml in methanol) and 3 ml chloroform. The mixture was vortexed f or 1 min and centrifuged at 1000×g for 10 min. The aqueous phase was discarded and the organic phase was transferred to another tube and evaporated to dryness in a speed-Vac concentrator. The residue was reconstituted in 100 $\mu$l methanol and 1 $\mu$l was injected onto a Varian 3400 gas chromatograph.

Quantitation

The quantitation of (R,S)-IFF, (R)-IFF, and (S)-IFF was performed in the selected ion mode at m/z 211 [(R)-IFF and (S)-IFF] and m/z 211 (IS). Standard solutions were prepared in drug-free plasma with TFF concentrations of 0.25–120 $\mu$g/ml. Two standard curves were used, one between 0.25 and 10 $\mu$g/ml and a second one from 10 to 150 $\mu$g/ml. For each standard curve, the coefficient correlation was 0.99.

The limit of detection was 125 mg/ml. The recovery and precision were good. The interassay precision was 5%. The peak area internal standard ratios of the compounds were used to calculate the concentrations for the standard curves and unknown samples.

Animal Pharmacokinetic Studies

The pharmacokinetics of (R,S)-IFF, (R)-IFF, and (S)-IFF were determined from female Fischer rats (F344, Charles River Canada) weighing 150–180 g. These animals were treated with a single i.v. dose of IFF,(R)-IFF, and (S)-IFF (125 mg/kg) dissolved in sterile water by the lateral tail vein. The rats were anesthetized with methan, and the carotid artery cannulated and fitted with a heparin lock. Blood samples (0.3–0.5 ml) were collected at 0, 5, 15, 30, 60, 90, 120, 180, 240 and 300 min. The collected plasma was centrifuged and stored at −20° C. until analysis.

The AUC (area under plasma concentration-time curve) was calculated by the trapezoidal method. The values were subjected to an analysis of variance comparison. The extrapolated AUC was estimated as the last measured plasma concentration divided by the terminal elimination rate constant.

Animal Model and Tumor Cells

MatB cells are maintained in vitro in α-minimum essential medium (GIBCO, Grand Island, N.Y.) supplemented with 1.3% sodium pyruvate, 2.6% glutamine, 1.3% non-essential amino acids, 10% fetal calf serum, and 100 units/ml gentamicin. Cells are maintained at 37° C. under 5% $CO_2$. A suspension of $5 \times 10^5$ cells is injected s.c. into the flanks of female F344 rats weighing 160–200 g. Within 7–10 days, when there is a palpable nodule, the rats are lightly anesthetized with ether, and a single i.v. dose of ifosfamide is injected via the tail vein. The tumor size and animal weights are monitored every other day. On the basis of the conventional rat human dose conversion factor of 1:7 and idealised human body weights and surface areas of 70 kg and 1.5 $m^2$, the dose of 100 mg/kg in the rat represents approximately 600 $mg/m^2$ in humans, which is in the general range of clinical single doses, as described by De Kraker, supra. Statistical analysis was performed using an impaired Student's s test or Pearson's $\chi^2$ analysis.

Determination of Myelotoxicity

For the studies of myelotoxicity, at least three animals/groups had blood obtained by cardiac puncture with a 23-gauge needle. The samples were heparinized and both WBC and platelet counts were determined using a Coulter Counter.

There were differences resulting in the presence of a tumor in these animals with regard to the effects of these treatments, and the data are therefore presented for each situation separately.

Lethality (Non-Tumor Bearing)

The toxicity was assessed by lethality within 7–10 days after administration of (R)-, (S)-, or (R,S)-ifosfamide in non-tumor-bearing Fischer 344 rats. At 100 and 125 mg/kg, there was minimal lethality in the (R)- and (R,S)-ifosfamide groups (1 of 5 and 1 of 5, respectively), whereas 0 of 5 rats died after the (S)-ifosfamide dosing. At 150 mg/kg, there was increased toxicity in the (R)- and (R,S)-IFF-treated groups, where 2 of 4 rats died in each of the groups, while 0 of 4 died in the (S)-IFF group. At this dose level, the lethality was apparently greater for the (R)-IFF-treated animals compared to either of the other groups (P=0.045).

Lethality (Tumor-Bearing)

At 100 mg/kg, there were 0 of 5 toxic deaths after treatment with (R,S)- or (S)-IFF, respectively, while (R)-IFF resulted in 1 of 5 animals dead. At 125 mg/kg, there were 4 of 10 and 5 of 10 toxic deaths after (R,S)- and (R)-IFF, respectively, and 2 of 10 after (S)-IFF treatment. $\chi^2$ analysis shows that there is a significant difference comparing treatment with (R)-IFF to (S)-IFF (P=0.017); however, there is no difference comparing either (R)-IFF or (S)-IFF to (R,S)-IFF. At 150 mg/kg, there were 5 of 5 deaths after either (R,S)- or (R)-IFF, and 3 of 5 after (S)-ifosfamide. This is no significant difference for the (R)-IFF versus either (S)-IFF or (R,S)-IFF (P=0.067).

Bone Marrow suppression

Figure 1B:
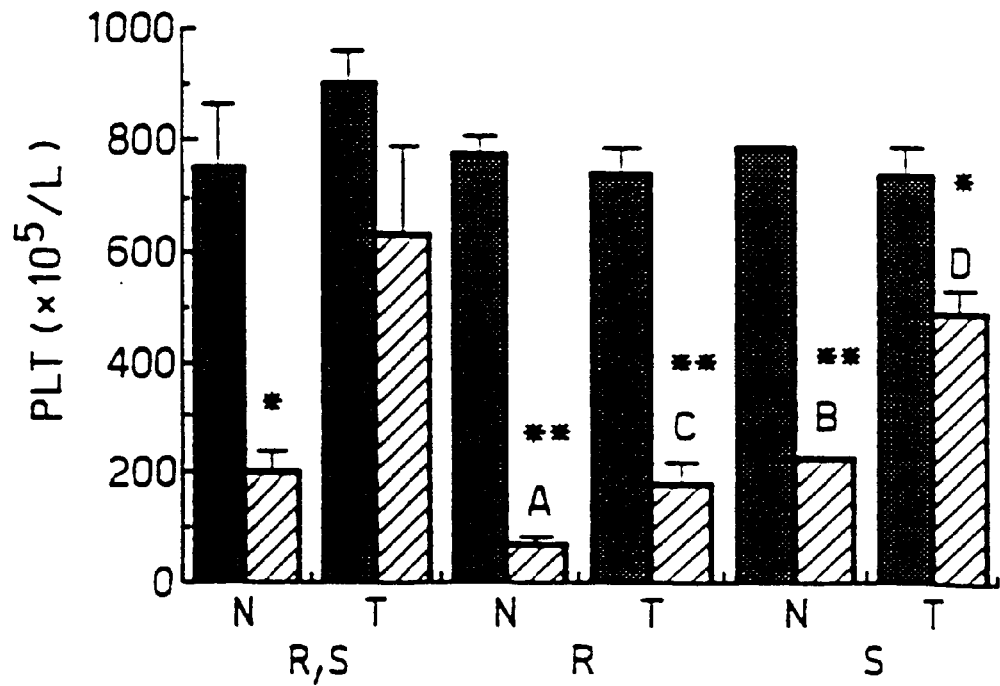

FIG. 1 demonstrates the results of measurement of WBC (FIG. 1A) and platelet (FIG. 1B) counts in blood obtained by cardiac puncture in non-tumor-bearing and tumor-bearing rats. Measurements were made prior to and 1 week after i.v. injection of 125 mg/kg of (R,S)-, (R)-, or (S)-ifosfamide. In tumor-free rats, myelosuppression is observed after all three formulations, although myelosuppression due to (S)-IFF is not statistically significant. In the presence of a tumor, the effects of a colony-stimulating factor are evidenced by higher WBC even prior to drug administration. Because the WBC progressively rises over time with exposure to the tumor, the intergroup variation in absolute WBC relates to differences in time from tumor inoculation to baseline WBC measurement and then drug administration. While both (R,S)- and (R)-IFF treatments result in significant myelosuppression, there is no such effect after (S)-IFF where the WBC is higher.

Differences in platelet toxicity are demonstrated in FIG. 1B. There is no tumor-induced effect on platelet counts, as is the case with most of the presently identified colony-stimulating factors. There is significant thrombocytopenia 1 week after administration of all 3 drug forms in non-tumor-bearing rats; however, (R)-ifosfamide resulted in greater platelet suppression that was statistically different from either the (R,S)- or the (S)-ifosfamide (P<0.05). Platelet suppression in the presence of tumor is significantly less after (S)-compared to either (R)- or (R,S)-ifosfamide.

Weight Loss

Weight loss was determined by every-other-day measurements of groups of at least three rats. Although the effect of (R)-IFF appears greatest, it is significantly so only at one time point. The weight loss effects do not correlate with the lethality at this dose, so that while the presence of the (R)-IFF does appear to result in greater weight loss at some time points, at this dose (125 mg/kg) it does not translate into greater animal death rate.

Pharmacokinetics

As detected in rat plasma after injection of 100 mg/kg i.v., there were statistically significant differences between $AUC_{RS}$ and $AUC_S$ (P<0.01) and $AUC_R$ versus $AUC_S$ (P<0.01), while no statistically significant difference was observed between $AUC_{RS}$ and $AUC_R$. These results are consistent with those obtained for toxicity and efficacy and indicate that (R)-IFF is metabolized to a greater degree than (S)-IFF via the activation pathway. This is the reverse of the N-dechloroethylation pathways where (S)-IFF is metabolized to a greater extent than (R)-IFF. However, N-dechloroethylation takes place at a slower rate than 4-hydroxylation and to a lesser extent.

Antitumor Activity. The wild-type MatB tumors are responsive to ifosfamide. While tumors in saline-treated rats continue to grow, in all treatment groups there was complete disappearance of measurable tumors within 14 days. In order to assess differences among the isomers in antitumor effects at the same dose, a MatB subline selected for resistance to nitrogen mustards was grown in the rats, which are at least 4-fold resistant to another nitrogen mustard, melphalan, in vivo. All three formulations resulted in equivalent significant tumor growth delay; there is no difference among the formulations regarding tumor growth duration.

The results of this study show no significant difference in the antitumor efficacy of (R)-IFF and (S)-IFF relative to (S)-IFF. The pharmacokinetics also indicated that (R)-IFF was cleared more quickly than (S)-IFF. Since the N-dechloroethylation pathway has been shown to be enantioselective for (S)-IFF and since the N-dechloroethylated metabolites are neither lethal or myelotoxic, it appears that more of the (R)-IFF is passing through the 4-hydroxylation pathway leading to the production of the cytotoxic metabolites.

We claim:

1. A method for treating cancer sensitive to the compound below in a human patient, with reduced CNS side-effects, which comprises the administration to said patient of an anti-cancer effective amount of dexifosfamide, substantially free of levoifosfamide.

* * * * *